United States Patent [19]

Bickelhaupt et al.

[11] Patent Number: 4,850,974
[45] Date of Patent: Jul. 25, 1989

[54] DISPENSER AND METHOD FOR AN ELONGATED FLEXIBLE MEMBER

[75] Inventors: Roger Bickelhaupt, Orange; Michael D. Rold, Costa Mesa, both of Calif.

[73] Assignee: Baxter International Inc., Deerfield, Ill.

[21] Appl. No.: 99,097

[22] Filed: Sep. 21, 1987

Related U.S. Application Data

[62] Division of Ser. No. 659,702, Oct. 11, 1984, Pat. No. 4,713,059.

[51] Int. Cl.[4] .............................................. A61M 5/00
[52] U.S. Cl. .................................................... 604/171
[58] Field of Search ..................... 242/99, 107.6, 84.8; 604/159, 171; 33/138, 137 R

[56] References Cited

U.S. PATENT DOCUMENTS

| | | | |
|---|---|---|---|
| 779,245 | 1/1905 | Stark | 272/99 |
| 3,055,361 | 9/1962 | Ballard | 604/162 |
| 3,185,151 | 5/1965 | Czorny | 604/163 |
| 3,335,723 | 8/1967 | Waldman, Jr. | 604/163 |
| 3,482,798 | 12/1969 | Kawaguchi | 242/99 |
| 3,561,445 | 2/1971 | Katerndahl | 604/159 |
| 3,711,734 | 1/1973 | Moe | 604/159 |
| 3,878,835 | 4/1975 | Utsugi | 604/159 |
| 3,982,544 | 9/1976 | Dyck | 604/159 |
| 3,995,628 | 12/1976 | Gula et al. | 604/159 |
| 4,160,451 | 7/1979 | Chittenden | 604/159 |
| 4,342,313 | 8/1982 | Chittenden | 604/159 |
| 4,397,091 | 8/1983 | Gustavsson et al. | 604/159 |
| 4,515,597 | 5/1985 | Frankhouser | 604/163 |
| 4,637,404 | 1/1987 | Gessman | 128/786 |

Primary Examiner—Edward M. Coven
Assistant Examiner—T. Brown
Attorney, Agent, or Firm—Debra E. Dahl; Gordon Peterson

[57] ABSTRACT

A dispenser comprising a base and a reel rotatably mounted on the base. An elongated flexible member which is to be dispensed is wound on the reel, and a housing is provided for the reel and the flexible member. Interlocking members on the reel and the housing hold the reel against rotation in the housing. The reel has first and second sets of radially extending fingers at the periphery of the reel, with the first set of fingers being inclined relative to the second set of fingers. The flexible member is wound on the reel between the first and second sets of fingers.

13 Claims, 4 Drawing Sheets

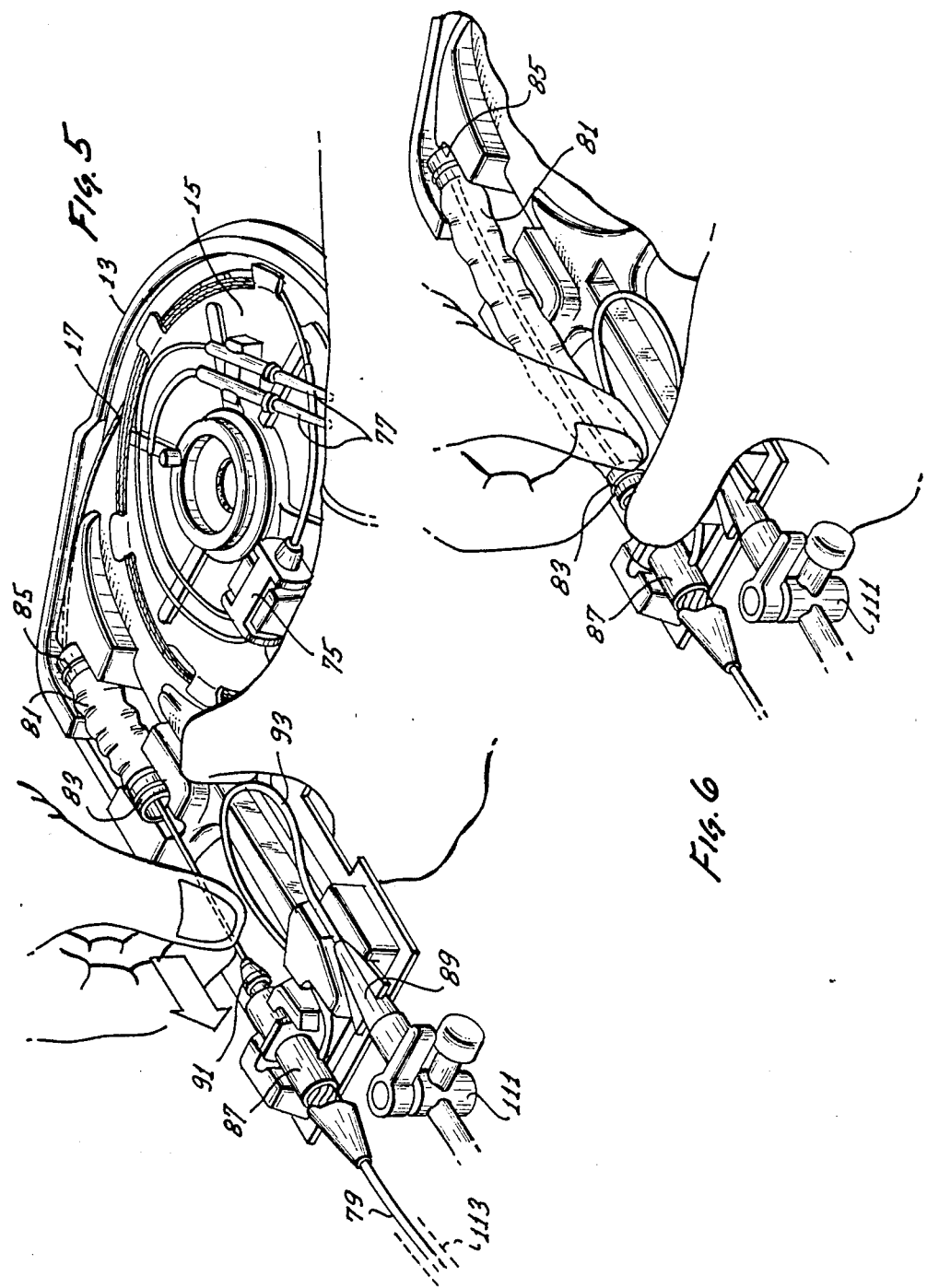

DISPENSER AND METHOD FOR AN ELONGATED FLEXIBLE MEMBER

This is a division of application Ser. No. 659,702, filed Oct. 11, 1984 and issued Dec. 15, 1987 and U.S. Pat. No. 4,713,059.

BACKGROUND OF THE INVENTION

Probes and catheters for insertion into the vascular system of a patient must be kept sterile during transit, storage and the ensuing medical procedure. Probes and catheters are typically enclosed in a sterile package at the manufacturer's plant and shipped to the user in the sterile package. When the probe or catheter is to be used, it is removed from the package and inserted into the patient's vascular system using conventional medical techniques. Unfortunately, after being removed from the sterile package, there is some risk of loss of sterility through contact with non-sterile objects. This risk is made somewhat greater by the elongated, flexible nature of probes and catheters.

SUMMARY OF THE INVENTION

This invention provides a dispenser for an elongated, flexible member, such as a probe or catheter, which enables the flexible member to be dispensed directly from the dispenser. Accordingly, insertion of the flexible member into the patient's vascular system is facilitated. In addition, the risk of loss of sterility is reduced because the flexible member can be inserted into the patient's vascular system directly from the dispenser.

A dispenser constructed in accordance with the teachings of this invention may include a base and a reel mounted on the base for rotation relative to the base. An elongated, flexible member to be dispensed is wound on the reel. A housing forms a sterile enclosure for the reel and flexible member.

To prevent entangling of the flexible member as a result of reel rotation within the enclosure, this invention provides cooperating means on the reel and the housing for holding the reel against rotation in the enclosure. The cooperating means is responsive to the removal of the housing to release the reel for rotation so that the flexible member can be dispensed. The cooperating means can advantageously include interlocking members on the reel and the housing. In addition, the dispenser preferably includes clamping means on the base and the housing for clamping a portion of the flexible member against longitudinal movement. This prevents back travel of the flexible member that could jam the reel.

To facilitate manufacturing of the reel and loading of the flexible member on the reel, the reel preferably has first and second sets of radially extending fingers at the periphery of the reel. The first set of fingers is inclined relative to the second set of fingers so that the flexible member can be wound on the reel between the two sets of fingers. To assure that the two sets of fingers remain inclined relative to each other, the base has a ring-like ledge, and the fingers of the first set ride on the ledge, and the fingers of the second set do not. Preferably, the fingers are resilient and resiliently bear on the shoulder.

The inner end portion of the flexible member may contain elements that are too large to be conveniently retained on or between the sets of fingers. Accordingly, the reel has a side face, and means is provided on the side face of the reel for releasably retaining the inner end portion of the flexible member. With this construction, the inner end portion of the flexible member can be readily retained even though it may be enlarged and include enlargements, such as plugs or connectors.

To further facilitate construction, the base and the reel are preferably integrally molded from plastic material. The reel can be advantageously snap fit onto a shaft molded integrally with the base. A resilient retainer retains the reel on the shaft and engages the reel to resist or retard free rotation of the reel.

The dispenser of this invention is preferably adapted for use in packaging and dispensing a sterile elongated, flexible member, such as a probe or catheter, although its use is not necessarily limited to this purpose. When used to dispense a probe or catheter, the housing is removed to free the reel for rotation. A portion of the probe or catheter which projects from the reel is introduced into the vascular system of the patient and, by pulling on such portion, the reel is rotated to unwind the probe or catheter from the reel to insert the probe or catheter farther into the vascular system. In this manner, the dispenser dispenses the probe or catheter directly into the vascular system. Accordingly, the risk of loss of sterility is greatly reduced.

The invention, together with additional features and advantages thereof, may best be understood by reference to the following description taken in connection with the accompanying illustrative drawings.

BRIEF DESCRIPTION OF THE DRAWINGS

FIGS. 5 and 6 are isometric views illustrating two steps in the use of the dispenser.

DESCRIPTION OF THE PREFERRED EMBODIMENT

Figure 1:
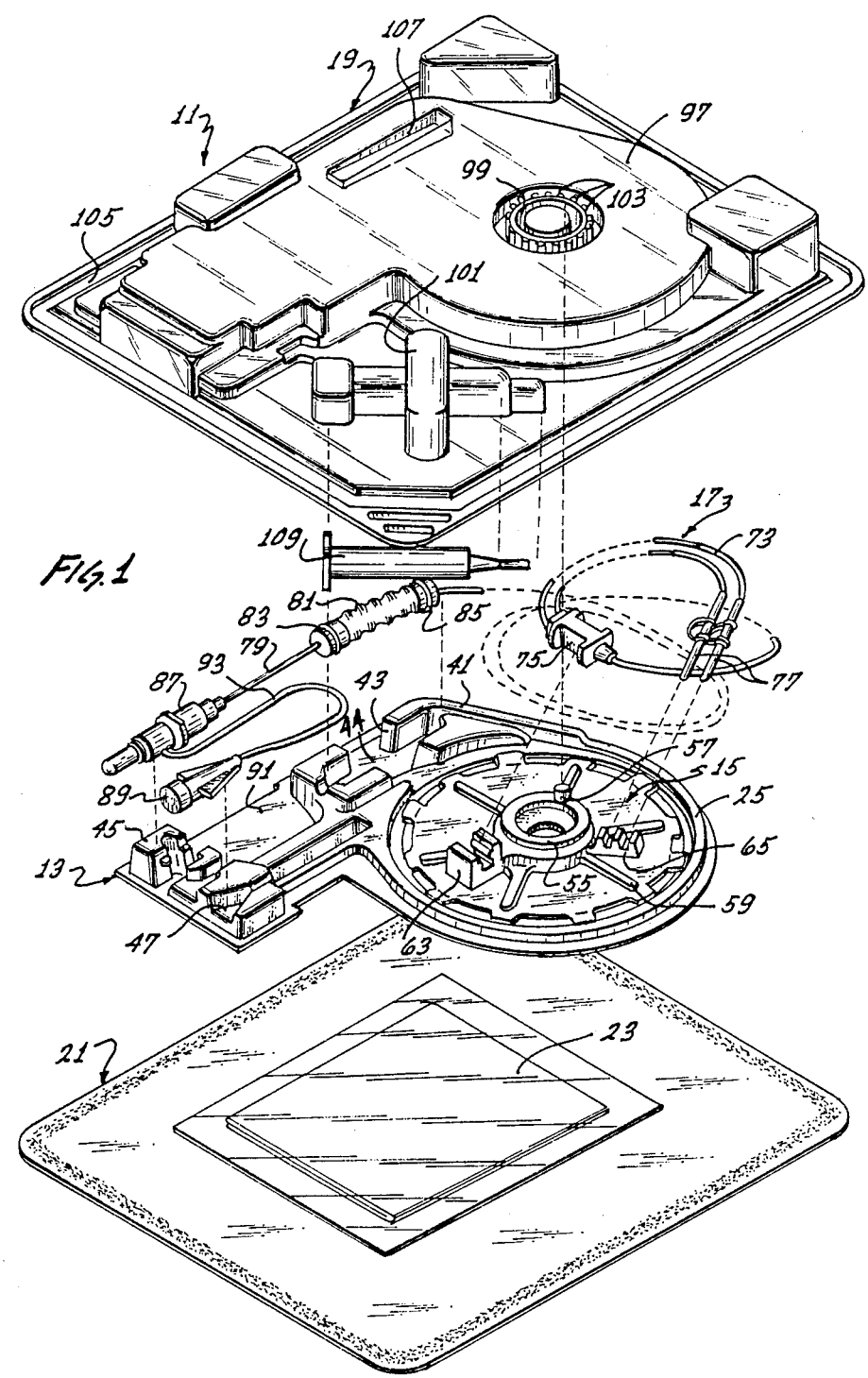
FIG. 1 is an exploded isometric view of one form of dispenser constructed in accordance with the teachings of this invention.

FIG. 1 shows a dispenser 11 which includes a base 13 and a reel 15 rotatably mounted on the base. The dispenser 11 may also be considered as including an elongated, flexible member in the form of a probe 17 wound on the reel 15 and projecting from it and housing means which includes a housing section or tray 19 and a cover 21. The housing section 19 and the cover 21 form an enclosure for the base 13, the reel 15, the elongated flexible probe 17 and a drape 23 which may be used in the insertion of the member 17.

The base 13 is constructed of plastic sheet material. Because the base 13 is rather intricately shaped, it is preferably integrally molded from plastic material.

Figure 3:
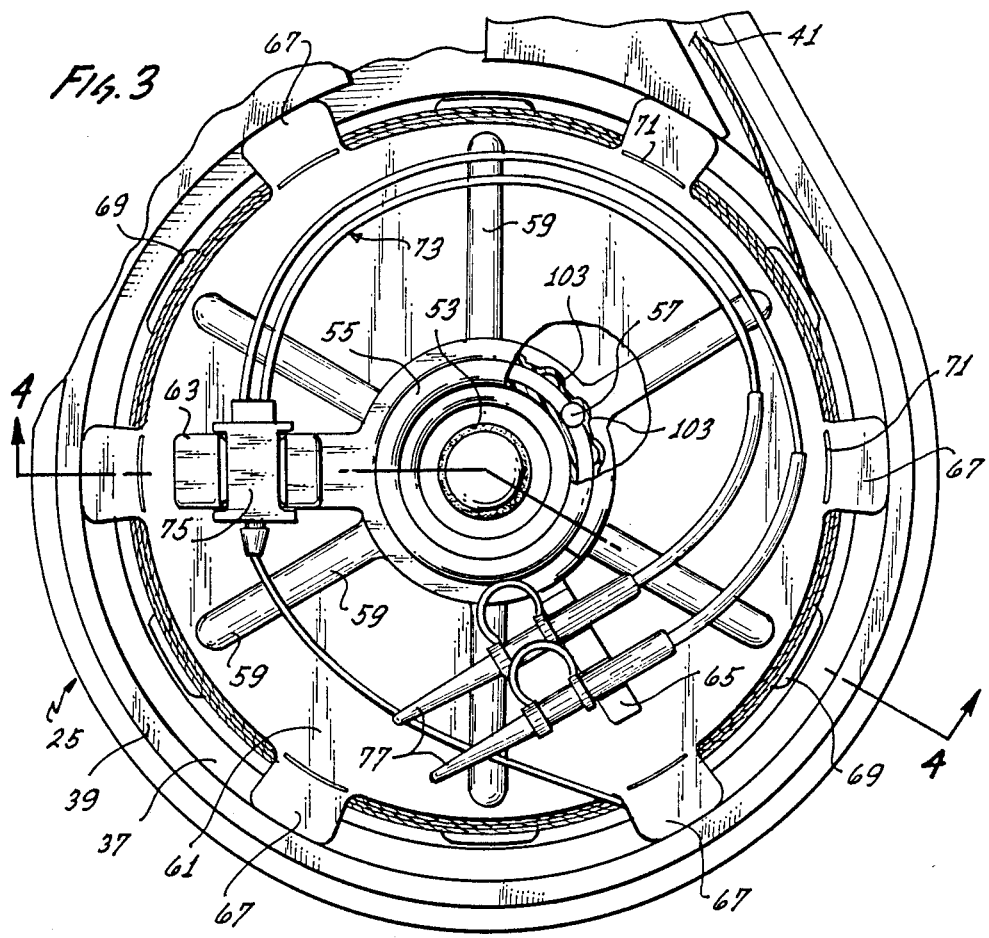
FIG. 3 is a fragmentary top plan view of a portion of the base, reel and probe.
Figure 4:
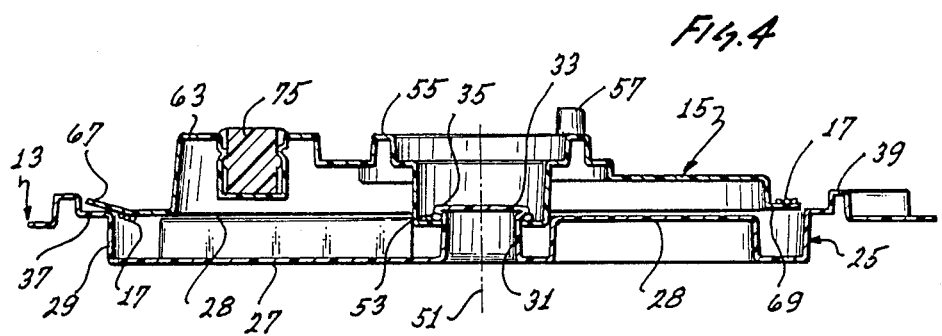
FIG. 4 is a sectional view taken generally along line 4—4 of FIG. 3.

As shown in FIGS. 1, 3 and 4, the base 13 has a storage or dished section 25 in which the reel 15 is mounted. The dished section 25 has an irregular floor 27 (FIG. 4) with raised portions 28, a cylindrical, peripheral wall 29 and a hollow, generally cylindrical shaft 31 coaxial with the peripheral wall. The shaft 31 has an end wall 33 which defines a circumferentially extending flange 35. An annular, ring-like ledge 37 is integrally joined to the upper (as viewed in FIG. 4) end of the peripheral wall 29 and is coaxial with the shaft 31. The ledge 37 is substantially surrounded by an upstanding hollow ring 39. The irregularities in the shape of the cross section of the base 13 as shown, for example, in FIG. 4, strengthen the base and permit it to be constructed from thin sheet material.

The base 13 has a track or groove 41 leading from the ledge 37 to a contamination sheath retainer 43, which has a floor 44 and which is partly formed by suitable raised portions of the base 13. The base 13 also has fitting retainers 45 and 47.

The reel 15 is formed of plastic sheet material and is preferably integrally molded. The reel 15 is mounted on the base 13 for rotational movement relative to the base about a rotational axis 51 (FIG. 4) coaxial with the shaft 31. For this purpose, the reel 15 has a central opening which enables it to be snap fit over the flange 35 of the shaft 31, and a resilient retainer 53 on the shaft below the flange 35 engages the reel to help prevent demounting of the reel from the shaft and to resist, but not prevent, rotation of the reel on the shaft 31. The reel 15 rides on the raised portions 28 of the base 13.

The reel 15 has a raised central hub 55 with one or more upstanding lugs 57 and raised radially extending strengthening ribs 59 on a side face 61 of the reel. A hollow, upstanding connector retainer 63 and terminal retainer 65 project upwardly from the side face 61.

The reel 15 has two sets of radially extending fingers 67 and 69 at the periphery of the reel with the first set of fingers 67 being longer radially than the shorter fingers 69. The fingers 67 and 69 are arranged in an alternating pattern as shown in FIG. 3, and the fingers 67 and 69 are inclined axially relative to each other. In the embodiment illustrated, the short fingers 69 are in an essentially radial plane just below the ledge 37, whereas the longer fingers 67 are inclined axially from the radial plane as shown by way of example in FIG. 4. The long fingers 67 are inclined upwardly and ride on the ledge 37, and this assures that the fingers 67 are inclined relative to the short fingers 69 and helps in the loading of the probe 17. The short fingers 69 terminate radially inwardly of the ledge 37. The long fingers 67 are resilient, and resiliently bear on the ledge 37. The resilience of the fingers 67 may be enhanced by lines of weakness 71 (FIG. 3) formed in the reel 15 at the base of each of the long fingers 67.

Figure 2:
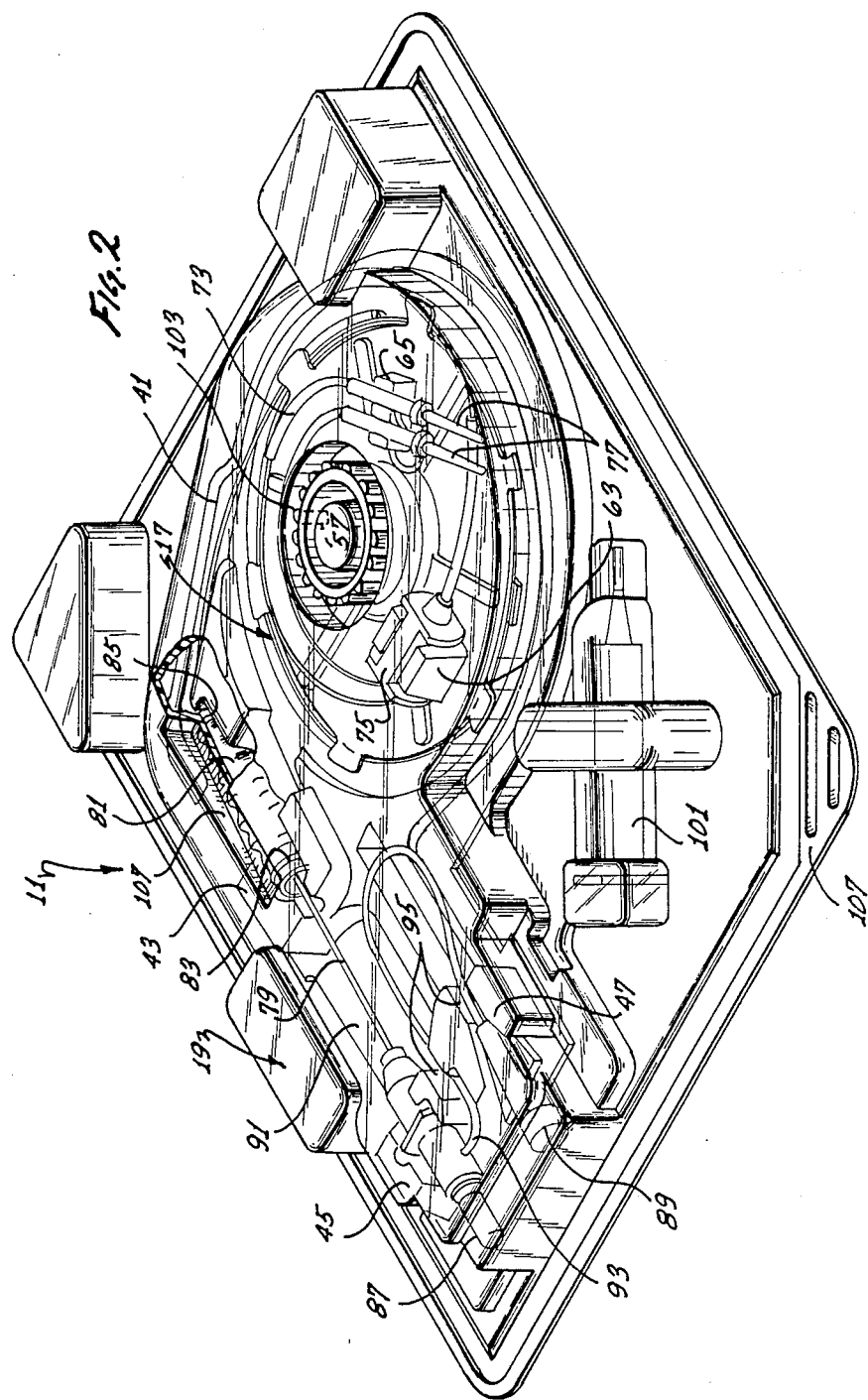
FIG. 2 is an isometric view of the dispenser.

Although the concepts of this invention can be applied to nonsterile flexible members, the invention is particularly adapted for use with sterile medical members. In the embodiment illustrated, the sterile pacing probe 17 is adapted for insertion into a patient and has an inner end portion 73 which includes a connector 75 and terminals 77 (FIGS. 1–3). Although the details of the probe 17 form no part of this invention, briefly, from the connector 75 proximally, the probe comprises a single flexible element and includes a flexible wire 79 extending through a flexible, axially expandable contamination sheath 81 having connectors 83 and 85 at its opposite ends. The probe 17 has a distal end (not shown) which is received within a Tuohy-Borst adapter 87, and a connector 89 is coupled to the adapter 87 by tubing 93. If desired, the member 17 may be a probe or any catheter of the type described in Swendson et al U.S. Patent application Ser. No. 434,318 filed on Oct. 14, 1982.

The connectors 75 and the terminals 77 are snap fit into, and retained by, the connector retainer 63 and the terminal retainers 65, respectively, as shown in FIGS. 1–4. From the connector 75 distally the probe 17 extends to the periphery of the reel 15 and beneath a first of the long fingers 67 (FIG. 3) over the top of the next short finger 69 and so on below the long fingers 67 and above the short fingers 69 several times around the periphery of the reel. The probe 17 can be easily wound on the reel 15 in this fashion by simply starting it beneath one of the long fingers 67 and rotating the reel. A portion of the probe 17 projects from the reel 15 through the track 41 and the contamination sheath 81. The contamination sheath 81 is held within the contamination sheath retainer 43 by virtue of a snap fit of the connectors 83 and 85 in the retainer 43. The wire 79 projects from the connector 83 across a shuttle space 91 between the retainers 43 and 45, and the adapter 87 is retained in the retainer 45. The connector 89 is retained in the retainer 47, and the tubing 93 is releasably retained in notches 95 formed in the base 13 (FIG. 2).

The housing section 19 which is preferably constructed of clear plastic sheet material and integrally molded includes a base cavity 97, a hub cavity 99 within the base cavity and a syringe cavity 101. The cavities 97 and 99 roughly conform to the outlines of the base 13 and the hub 55, respectively. The hub cavity 99 has a scalloped outer periphery defining a series of lugs 103. The housing section 19 also has a peripheral flange 105 and an inclined ramp 107.

In use, the probe 17 can be easily wound on the reel 15 as described above. The base 13 with the reel 15 and probe 17 attached to it are then placed in the tray cavity 97 such that the base 13 and the hub 55 are received within the tray cavity 97 and the hub cavity 99, respectively, and the lug 57 of the hub 55 fits within one of the scallops between the lugs 103 of the housing section 19 and interlocks with such lugs 103. The interlock formed by the lugs 57 and 103 holds the reel 15 against rotation. In addition, the ramp 107 and the wall 44 of the base 13 at the contamination sheath retainer 43 cooperate to clamp the contamination sheath 81 and the portion of the wire 79 extending therethrough against movement longitudinally of the probe 17. This prevents retrograde movement of the probe 17 that might remove the distal end of the probe from the adapter 87 and/or move the probe 17 toward the reel 15 to cause tangling of the probe. A syringe 109 (FIG. 1) may be provided in the syringe cavity 101, if desired.

To complete the packaging process, drape 23 is placed on the base 13, and the cover 21, which may be constructed of suitable plastic sheet material, is adhered, as by heat sealing, to the flange 105. The housing section 19 and the cover 21 cooperate to define a sterile enclosure for the base 13, the reel 15 and the probe 17, and all of these members so enclosed are also sterile. The dispenser 11 may be shipped and stored in this fully packaged condition.

Prior to using the dispenser 11, the cover 21 is removed from the housing section 19, and the base 13 with the reel 15 and probe 17 thereon are removed from the housing section. After completion of conventional preliminary procedures, including coupling the connector 89 to a three-way valve 111 (FIG. 5), a portion of the probe 17 which projects from the reel 15 is inserted into a previously positioned guiding catheter 113 (FIG. 5) into the vascular system to the heart of a patient. One example of a guiding catheter 113 for a pacing probe is shown in Swendson et al U.S. patent application Ser. No. 434,318 filed on Oct. 14, 1982.

One advantage of this invention is that the probe 17 can be advanced through the guiding catheter 113 and the vascular system of the patient, after conventional, preliminary medical procedures which form no part of this invention have been appropriately observed, by manually pulling the probe 17 forwardly in the space 91 as shown in FIG. 5. The advancing motion of the probe 17 can be carried out by the physician shuttling his fingers back and forth in the space 91. The reel 15 rotates on the shaft 31 relative to the base 13 to permit this advancing motion to occur. When the probe 17 has been advanced to the desired position, such as to a port (not shown) of the guiding catheter 113, the advancing motion is terminated, and the connector 83 is moved distally and attached to the adapter 87 as permitted by the contamination sheath 81 (FIG. 6) before the probe 17 is removed from the reel 15. The ability to advance the probe 17 as shown in FIG. 5 and to make the connection illustrated in FIG. 6 without removing the probe from the reel 15 facilitates the insertion process and reduces the likelihood of contamination of the probe. After the probe 17 is removed from the reel 15, the connector 85 is coupled proximally to the connector 75, and the procedure continues in accordance with conventional practice.

Although an exemplary embodiment of the invention has been shown and described, many changes, modifications and substitutions may be made by one having ordinary skill in the art without necessarily departing from the spirit and scope of this invention.

We claim:

1. A dispenser comprising:
   a base having a storage section, a contamination sheath retainer and a first fitting retainer, said retainers being outside said storage section;
   a contamination sheath in said contamination sheath retainer;
   a first fitting in said first fitting retainer;
   an elongated, flexible member having a first portion wound in said storage section and a second portion distally of said first portion extending through said contamination sheath and into said first fitting; and
   means for retaining said first portion of said member in said storage section.

2. A dispenser as defined in claim 1 wherein said retainers are spaced apart to define a shuttle space and said member extends across said shuttle space.

3. A dispenser as defined in claim 1 wherein the base has a second fitting retainer outside said storage section and including a second fitting in said second fitting retainer and tubing extending between said first and second fittings.

4. A dispenser as defined in claim 1 wherein said base is constructed of molded plastic material.

5. A dispenser as defined in claim 1 wherein said contamination sheath retainer has side walls with generally opposed openings therein.

6. A dispenser as defined in claim 1 wherein said contamination sheath retainer has a floor and includes portions of the base raised from said floor.

7. A dispenser as defined in claim 1 wherein said storage section includes a dished section of said base, said dished section having an opening leading to said contamination sheath retainer.

8. A dispenser comprising:
   a base having a storage section and first and second retainers outside said storage section and spaced apart to define a shuttle space;
   first and second fittings retained in said first and second retainers, respectively;
   an elongated, flexible member having a first portion wound in said storage section and a second portion distally of said first portion extending through said first retainer, across said shuttle space and into the second retainer; and
   means for retaining said first portion of said member in the storage section.

9. A dispenser as defined in claim 8 wherein the base has a second fitting retainer outside said storage section and including a second fitting in said second fitting retainer and tubing extending between said first and second fittings.

10. A dispenser as defined in claim 8 wherein said base is constructed of molded plastic material.

11. A dispenser as defined in claim 8 wherein said storage section includes a dished section of said base, said dished section having an opening leading to said first retainer.

12. A method of inserting an elongated flexible medical member into a vascular system of a patient comprising:
   providing a dispenser which includes a base having a storage section, a contamination sheath retainer, a shuttle space and a first fitting retainer, said retainers and said shuttle space being outside said storage section with a first portion of said member wound in the storage section and with a second portion of said member projecting from said storage section through a contamination sheath in said contamination sheath retainer, across the shuttle space and through a first fitting in said first fitting retainer;
   introducing said second portion of said member into said vascular system of the patient; and
   pulling on said member in said shuttle space with a shuttle motion to unwind said first portion of said member in said storage section and to advance said member farther into said vascular system of said patient.

13. A method as defined in claim 12 wherein after advancing said member into said vascular system of the patient, said contamination sheath is attached to said first fitting.

* * * * *